United States Patent [19]

Schmukler et al.

[11] Patent Number: 5,671,754

[45] Date of Patent: Sep. 30, 1997

[54] VIRAL-PROOFING A PROTECTIVE BARRIER

[75] Inventors: Robert Schmukler, Rockville; C. David Lytle, Laytonsville, both of Md.

[73] Assignee: The United States of America as represented by the Department of Health and Human Services, Washington, D.C.

[21] Appl. No.: 353,164

[22] Filed: Dec. 9, 1994

Related U.S. Application Data

[63] Continuation of Ser. No. 906,716, Jun. 30, 1992, abandoned.

[51] Int. Cl.$^6$ ........................................ A61F 6/04
[52] U.S. Cl. ........................ 128/844; 128/918; 128/832
[58] Field of Search ........................... 128/917, 918, 128/834, 837, 830, 832, 833, 842, 844

[56] References Cited

U.S. PATENT DOCUMENTS

| | | | |
|---|---|---|---|
| 3,876,757 | 4/1975 | Scherm | 424/44 |
| 4,200,090 | 4/1980 | Drubish | 128/832 |
| 4,323,548 | 4/1982 | Scherm | 424/44 |
| 4,393,871 | 7/1983 | Vorhauer et al. | 604/58 X |
| 4,499,154 | 2/1985 | James et al. | 2/168 X |
| 4,511,558 | 4/1985 | Shur | 514/8 |
| 4,858,624 | 8/1989 | Shibata | 128/834 |
| 4,922,928 | 5/1990 | Burnhill | 128/832 |
| 4,977,188 | 12/1990 | Kneen et al. | 514/575 |
| 4,988,733 | 1/1991 | Sulmon et al. | 514/575 |
| 5,036,157 | 7/1991 | Kneen et al. | 562/623 |
| 5,045,341 | 9/1991 | Shlenker | 128/844 X |
| 5,089,205 | 2/1992 | Huang et al. | 264/255 |
| 5,338,565 | 8/1994 | Shlenker et al. | 128/844 X |

FOREIGN PATENT DOCUMENTS

| | | | |
|---|---|---|---|
| 0 136900 | 4/1985 | European Pat. Off. | |
| 0 141628 | 5/1985 | European Pat. Off. | |
| 1046465 | 2/1989 | Japan | 128/918 |
| 9007876 | 7/1980 | WIPO | |
| 8904647 | 6/1989 | WIPO | 128/918 |
| 9007876 | 7/1990 | WIPO | |
| 9112796 | 9/1991 | WIPO | |

*Primary Examiner*—Danton D. DeMille
*Attorney, Agent, or Firm*—Spencer & Frank

[57] ABSTRACT

A method of preventing charged particles from passing through holes in a barrier material which involves surface treating a barrier material with an ionic surfactant to impart a charge to the barrier material. In a preferred embodiment, prophylactics such as condoms and surgical gloves can be treated with an anionic surfactant. Tests have confirmed that such surface treated articles can repel virus particles such as human immunodeficiency (HIV) virus, hepatitis B virus and herpes simplex virus (HSV). Ionic surfactant treated articles include prophylactics such as condoms and diaphragms, gloves, including surgical gloves, surgical masks, respiratory masks and filters, filters, including membrane, and wound dressings, including bandages.

14 Claims, 1 Drawing Sheet

FIG. 1
FIG. 2
FIG. 3
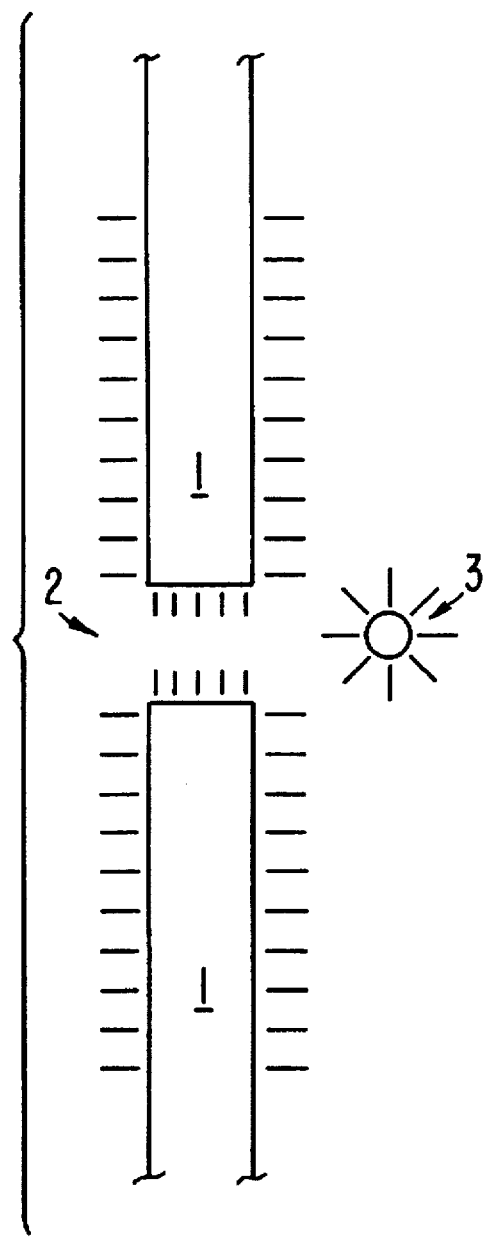
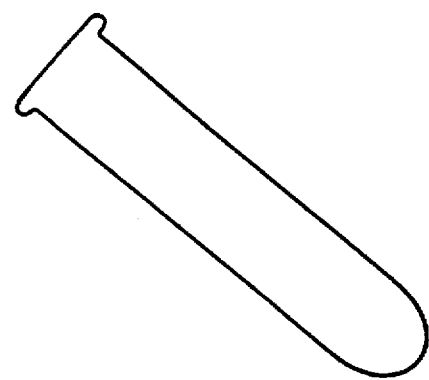
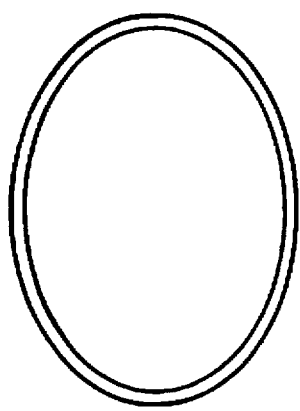

VIRAL-PROOFING A PROTECTIVE BARRIER

This application is a continuation of application Ser. No. 07/906,716 filed Jun. 30, 1992, now abandoned.

TECHNICAL FIELD

The present invention relates to protective barrier materials. More particularly, the present invention relates to methods of treating protective barrier materials so that viruses are prevented from passing through the barrier materials.

BACKGROUND ART

With the emergence of the AIDS health crisis and related concerns, the effectiveness of barrier materials, including elastic polymers such as latex, the prevalent condom and glove material, has come into question. The failure of barrier materials due to manufacturing defects has been the subject of previous investigations. Presently, barrier materials, such as condoms and gloves, are tested for manufacturing defects.

A new concern regarding barrier materials is their ability to block the passage of pathogenic viruses which may be so small as to pass through holes in barrier materials which cannot be readily detected. Presently, all tests of barrier integrity have a minimum sensitivity for the detection of holes sizes which are much larger than viruses.

There exists a need for a method of ensuring that barrier materials can effectively block the passage of pathogenic viruses through holes or pores which may be undetectable by standard tests.

DISCLOSURE OF THE INVENTION

It is accordingly one object of the present invention to provide barrier materials which block the passage of viruses therethrough.

Another object of the present invention is to provide barrier materials which repel viruses.

A further object of the present invention is to provide barrier materials which have charged surfaces.

A still further object of the present invention is to provide a method of producing barrier materials which block the passage of viruses therethrough.

An even further object of the present invention is to provide a method of treating barrier materials in such a manner so that they repel viruses.

A yet further object of the present invention is to provide a method of treating barrier materials so that they have charged surfaces.

According to these and further objects of the present invention which will become apparent as the description thereof proceeds, the present invention provides for a method of preventing charged particles from passing through holes in a barrier material which involves:

providing a barrier material; and surface treating the barrier material with an ionic surfactant to impart a charge to the barrier material.

The present invention further provides for a method of viral-proofing a protective barrier which involves:

providing a protective barrier; and surface treating the protective barrier with an ionic surfactant to impart a charge to the protective barrier which effects electrostatic forces between the protective barrier and viral particles.

The present invention also provides an article comprising an ionic surfactant treated barrier material having a surface charge.

BRIEF DESCRIPTION OF DRAWINGS

FIG. 1 depicts the surface treatment of a barrier material effectively reducing the size of a pore or hole in the barrier material in accordance with the subject invention.

FIG. 2 depicts a condom formed of a barrier material which may be treated in accordance with the subject invention.

FIG. 3 depicts a diaphragm formed of a barrier material which may be treated in accordance with the subject invention.

BEST MODE FOR CARRYING OUT THE INVENTION

The present invention is directed to methods of chemically treating barrier materials so that the barrier materials effectively block the passage of minute particles therethrough, regardless of the presence of undetected holes or pores in the barrier materials.

The basic principle of the present invention involves providing the surface of barrier materials with a charge so that individual particles, having a like charge are repelled from the barrier material. Preferably, in the treating process, both the surface of the barrier material and the interior surfaces of any and all holes and pores in the barrier material are likewise treated so as to have a charge.

In addition to repelling like-charged particles, it has been determined that the treated barrier materials will function to attract and bind opposite-charged particles which may be present. This feature becomes significant when opposite-charged particles become bound within holes and/or pores and thus reduce the size or diameter of the holes or pores and eventually block the holes or pores.

The chemical treatment of the barrier materials preferably provides the barrier materials with a permanent or semipermanent charge. In most cases, the barrier materials are used in articles such as condoms and surgical gloves which are discarded after use. In such articles, a semipermanent chemical treatment is sufficient. In other applications, such as filters a permanent charge on the surface of the barrier material may be more desirable, especially in situations in which the barrier material is used for an extended period of time or reused.

Specific applications for which the present invention was developed include barrier materials conventionally utilized to prevent the transmission of viruses and bacteria, including prophylactics such as condoms and diaphragms, gloves, including surgical gloves, surgical masks, respiratory masks and filters, filters, including membrane, wound dressings, including bandages, and the like. An exemplary condom and diaphragm are respectively shown in FIGS. 2 and 3. From this partial list of articles, it can be appreciated that virtually all types of barrier materials can be treated according to the present invention including natural and synthetic polymers, natural and synthetic rubbers, e.g., latex, woven and/or matted natural and synthetic fabrics, etc. While the present invention was primarily developed to ensure that viruses would not pass through undetectable holes or pores in condoms and surgical gloves, charged surfaces on more porous articles, such as surgical and respiratory masks and filters provide similar benefits of repelling like-charged particles, such as bacteria and viruses, and binding opposite-charged particles. When the concept of the present invention is applied to filters, including membrane filters, these treated filter can be used to selectively filter out charged particles from a fluid.

For illustrative purposes, the present invention is described as being effective for blocking the passage of bacteria and viruses through barrier materials. Nevertheless, it is to be understood that the principles of the present invention are applicable to all particles which bear a charge.

The method of treating the surface of a barrier material according to the present invention involves contacting the barrier material with an anionic or cationic surfactant which binds strongly to the barrier material surface. The barrier material can be contacted with the anionic or cationic surfactant in any convenient manner including spraying, dipping, or the like. For products or articles such as condoms and surgical gloves, which are subjected to "wet" quality assurance testing at the end of their production process(es), the anionic or cationic surfactant can be added to the wet testing fluid and thus serve a dual function. As a wetting agent the surfactant would make the acceptance test more sensitive for the detection of holes. At the same time, the product or article would receive the desired surface treatment. In the case of latex and similar boundary materials which are hydrophobic, the use of a surfactant in "wet" tests is essential to ensure that wetting of the complete surface together with all potential holes occurs. Moreover, the use of a surfactant results in rapid wetting, thus expediting "wet" testing processes.

Any ionic surfactant which imparts a charge to the barrier materials can be utilized in the method of the present invention. The surfactant should be chosen to impart a charge to the surface of the barrier material which is the same as the charge of particles which are to be blocked by the barrier material. In this regard, anionic surfactants have been found to impart a negative charge to barrier materials and cationic surfactants have been found to impart a positive charge to barrier materials.

In addition to the above considerations, the surfactant should also be chosen to be resistant to removal from the barrier surface in the physiologic environment. In this regard, it has been found that contacting barrier materials with surfactants and subsequently drying the treated barrier materials provides sufficient adhesion of the surfactants to the barrier materials. Surfactants which are known to be biocompatible for skin and mucous membranes such as, for example, dodecylsulfate, are preferred for use on barrier materials used in the manufacture of condoms, diaphragms, wound dressings and surgical gloves. Less biocompatible surfactants, may be used on articles which are not intended to come into contact with skin and mucous membranes. According to one embodiment of the present invention, a mixture of anionic or cationic surfactants can be utilized.

FIG. 1 shows how the surface treatment of a barrier material effectively reduces the size of a hole or pore in the barrier material. In FIG. 1, the barrier material 1 which has been treated with an anionic surfactant is shown as having a through-hole 2 therein. Negative charges on the surface of the barrier material 1, including on the inner surface of hole 2 are depicted as minus signs ("−"). Due to the nature of surfactants and their ability to wet surfaces, the surfactant coats every exposed surface of the barrier material 1 including the inner surfaces of holes 2 and pores.

A negative-charged particle 3, e.g., a virus, is shown in proximity to the barrier material 1. Due to the fact that the particle 3 has a like-charge to that imparted to the surface of the barrier material 1 by surfactant treatment, the particle 3 will be repelled from the barrier material 1 by electrostatic forces. In studies, it has been determined that the electrostatic forces are sufficient to repel the particles from the barrier material even in the presence of positive pressure gradients.

The relative size of the particles to the diameter of holes or pores in the barrier material does not appear to have an adverse effect in the desired manner in which the particles are repelled. It was generally accepted that a virus particle may pass through a hole whose diameter is greater than the diameter of the particle measured from electron micrographs. More recently, the effective or hydraulic diameters of several virus particles have been found, this produces a means of determining the size of holes in barrier materials which will allow the viral particles to pass through the barrier materials. Previous investigations in the effective or hydraulic diameters of several virus particles verify that viruses in solution, because of their boundary layers, may require larger diameter holes to pass through than comparable dry viruses.

FIG. 1 depicts a negative-charged particle and a barrier material which has been chemically treated with an anionic surfactant to produce a negative-charged surface. As discussed above, a similar result or effect could be provided by treating a barrier material with a cationic surfactant to repel positive-charged particles. Of course, for particles of a similar mass, those which have a stronger charge will be more subject to electrostatic forces.

Features and characteristics of the present invention will be discussed with reference to the following example, to which the present invention is not to be considered limited.

EXAMPLE

In this example polycarbonate filters with well-defined holes were surface treated with anionic surfactants and tested to determine how the surfactant treatment effected the transmission of surrogate viruses through the filters. For safety considerations, bacteriophages were used as surrogate viruses for human pathogenic viruses, e.g., human immunodeficiency virus (HIV), hepatitis B virus, or herpes simplex virus (HSV). The viruses, their host cells and their compositions are listed in Table 1 below. The membrane-containing bacteriophages φ6 and PRD1 were chosen as possible surrogates for HIV-1 and hepatitis B which both have a membrane envelope.

TABLE 1

| Virus | Host Cell | Virus Composition |
|---|---|---|
| φX174 | Escherichia coli C | ssDNA, protein |
| T7am28 | E. coli O11 | dsDNS, protein, short tail |
| PRD1 | Salmonella typhimurium LT2 | dsDNS, protein, internal lipid |
| φ6 | P. phaseolicola | dsRNA, protein, external lipid | ss = single stranded; ds = double stranded

The virus suspensions were tested at concentrations of $0.4 \times 10^4$ to $1.5 \times 10^4$ PFU/ml. The viruses in 3 ml of Dulbecco's phosphate-buffered saline were filtered through 25-mm Nuclepore polycarbonate membrane filters with quoted pore diameters of 0.1μ and 0.2μ. The pore diameters quoted by the manufacturer define the maximum pore diameter, with the median diameter being approximately 10% less than the quoted value. The filtration rate was controlled by attaching a hypodermic needle to the downstream side of the filters and pushing the needle into a Vacutainer. Virus titers were determined before and after filtration and the fractions which passed through the filters were calculated by conventional virologic methods.

The results of transmission tests are shown in Table 2. Also shown in Table 2 are the diameters of the viruses as measured by electron microscopy for comparison with filter hole size.

TABLE 2

VIRAL PROOFING OF BARRIERS (EXPERIMENTAL)
Fraction Transmitted Through Filters (1.0 = 100%)

| Filter | Viruses | | | |
|---|---|---|---|---|
| | φX | T7 | PRD1 | φ6 |
| .1µ Control PVP Treated | .94 ± .05 | 1.19 ± .13 | .94 ± .07 | 1.15 ± .11 |
| .1µ SDS Treated | .23 ± .06 | .19 ± .04 | .0024 ± .0016 | .006 ± .005 |
| .1µ Texapon ASV | 1.13 ± .01 | .88 ± .04 | .027 ± .008 | .17 ± .06 |
| .2µ Control PVP Treated | .92 ± .06 | 1.20 ± .15 | 1.11 ± .03 | 1.17 ± .07 |
| .2µ SDS Treated | .52 ± .08 | .44 ± .15 | .17 ± .07 | .19 ± .09 |
| .2µ Texapon ASV | 1.22 ± .02 | .82 ± .03 | .17 ± .07 | .16 ± .04 |
| SEM Size | .027µ with protein coat | .065µ + .017µ tail with protein coat | .065µ internal membrane and external protein | .08µ external lipid membrane with protein sticking out |

PRD 1 & φ6, because of lipid membranes are closest surrogate viruses to HIV and Hepatitus B, which both have a membrane envelope
PVP = Polyvinylpyrolidone - Non-ionic surfactant normally used on filters, biocompatible
SDS = Sodium dodecyl sulfate anionic surfactant, PVP free filters treated with SDS solution
Texapon ASV = Shampoo concentrate, meets FDA safety standards for skin and mucous membranes, manufactured by Henkel Corp.

In this example, treatment with the polyvinylpyrolidone (PVP) was used as a control since PVP is a non-ionic surfactant and therefore, does not impart any charge to the filters. The Texapon ASV is a commercially available anionic shampoo concentrate from Henkel Corp. The Texapon ASV was chosen because it meets FDA safety standards for skin and mucous membrane exposure. The filter sizes were chosen to ensure that, absent a charge on the filters, 100% of the virus particles could pass therethrough. As a comparison of the filter sizes, it is noted that current methods of hole detection have a limited lower detection range of about 20–40µ.

The results shown in Table 2 demonstrate that for the surrogate viruses of interest, i.e. PRD1 and φ6, the filter membranes treated with the sodium dodecylsulfate and Texapon ASV essentially prevented transmission of these surrogate viruses. The filter membranes treated with sodium dodecyl sulfate also significantly reduced the transmission of φx and T7 which are protein coated. As expected, viruses with membrane coatings which have a stronger particle charge due to the membrane coatings are more easily repelled by the treated filters.

Although the present invention has been described with reference to particular means, materials and embodiments, from the foregoing description, one skilled in the art can easily ascertain the essential characteristics of the present invention and various changes and modifications may be made to adapt the various uses and characteristics without departing from the spirit and scope of the present invention as described by the claims which follow.

What is claimed is:

1. A viral barrier comprising an ionic surfactant treated barrier material having a surface charge, wherein said ionic surfactant treated barrier material consists essentially of a layer of said barrier material and an ionic surfactant which is bonded directly to said layer of said barrier material, and said ionic surfactant provides said viral barrier with a surface charge which repels viruses so as to prevent ingress of viruses through said viral barrier.

2. A viral barrier according to claim 1, wherein said viral barrier is a prophylactic.

3. A viral barrier according to claim 2, wherein said prophylactic comprises a condom.

4. A viral barrier according to claim 2, wherein said prophylactic comprises a diaphragm.

5. A viral barrier according to claim 1, wherein said surfactant comprises a biocompatable surfactant.

6. A viral barrier according to claim 5 wherein said biocompatable surfactant comprises dodecylsulfate.

7. A viral barrier according to claim 1 wherein said barrier material is a polymeric material.

8. A viral barrier comprising an ionic surfactant treated barrier material having a surface charge, wherein said ionic surfactant treated barrier material consists essentially of a layer of said barrier material and an ionic surfactant which is bonded directly to said layer of said barrier material, wherein said ionic surfactant prevents ingress of viruses through said viral barrier solely by providing said viral barrier with a surface charge which repels or attracts viruses.

9. A viral barrier according to claim 8, wherein said viral barrier is a prophylactic.

10. A viral barrier according to claim 9, wherein said prophylactic comprises a condom.

11. A viral barrier according to claim 9, wherein said prophylactic comprises a diaphragm.

12. A viral barrier according to claim 8, wherein said surfactant comprises a biocompatable surfactant.

13. A viral barrier according to claim 12 wherein said biocompatable surfactant comprises dodecylsulfate.

14. A viral barrier according to claim 12 wherein said barrier material is a polymeric material.

* * * * *